United States Patent
Warlick et al.

(10) Patent No.: US 12,303,721 B2
(45) Date of Patent: *May 20, 2025

(54) ACOUSTIC SHOCK WAVE TREATMENT AND DEVICES FOR APPENDAGES

(71) Applicant: SoftWave Tissue Regeneration Technologies, LLC, Kennesaw, GA (US)

(72) Inventors: John F. Warlick, Woodstock, GA (US); Irwin Goldstein, San Diego, CA (US)

(73) Assignee: Softwave Tissue Regeneration Technologies, LLC, Kennesaw, GA (US)

( * ) Notice: Subject to any disclaimer, the term of this patent is extended or adjusted under 35 U.S.C. 154(b) by 115 days.

This patent is subject to a terminal disclaimer.

(21) Appl. No.: 18/196,643

(22) Filed: May 12, 2023

(65) Prior Publication Data

US 2024/0024704 A1 Jan. 25, 2024

Related U.S. Application Data

(60) Provisional application No. 63/391,938, filed on Jul. 25, 2022.

(51) Int. Cl.
*A61N 7/00* (2006.01)

(52) U.S. Cl.
CPC ........ *A61N 7/00* (2013.01); *A61N 2007/0004* (2013.01); *A61N 2007/0069* (2013.01)

(58) Field of Classification Search
CPC .... A61B 2090/0454; A61B 2090/0472; A61N 2007/0004; A61N 2007/0069; A61N 7/00; A61H 23/008

See application file for complete search history.

(56) References Cited

U.S. PATENT DOCUMENTS 6,066,123 A 5/2000 Li
6,368,292 B1 * 4/2002 Ogden ............... A61B 17/2256
601/2

(Continued)

FOREIGN PATENT DOCUMENTS

RU 2609054 C1 * 1/2017

OTHER PUBLICATIONS

Translated Copy of Vladimir RU 2609054 (Year: 2017).*
Reisman, "Initial experience with linear focused shockwave treatment for erectile dysfunction: A 6-month follow-up pilot study", 2014 (Year: 2014).*

(Continued)

*Primary Examiner* — Angela M Hoffa
*Assistant Examiner* — Brooke Lyn Klein
(74) *Attorney, Agent, or Firm* — David O. Simmons

(57) ABSTRACT

An improved method of treating an appendage of a patient using acoustic shock waves has the steps of: providing an appendage in need of an acoustic shock wave treatment; placing an acoustic shock wave applicator on a surface of the appendage; placing a gaseous filled membrane on an opposite surface of the appendage; activating an acoustic shock wave generator or source to emit acoustic shock waves from an acoustic shock wave applicator; and wherein the acoustic shock wave is transmitted from the acoustic shock wave applicator through the surface sending the emitted acoustic shock waves into the tissue of the appendage and exiting the opposite surface of the appendage to the gaseous filled membrane where a reflection of the acoustic shock wave occurs sending reflected acoustic shock waves back through the appendage.

17 Claims, 9 Drawing Sheets

(56) References Cited

U.S. PATENT DOCUMENTS

| | | | |
|---|---|---|---|
| 7,485,101 | B1 | 2/2009 | Faragalla |
| 7,601,127 | B2 | 10/2009 | Schultheiss et al. |
| 9,198,635 | B2* | 12/2015 | Crum ................... A61B 8/06 |
| 9,707,414 | B2* | 7/2017 | Kardosh .............. A61N 1/0597 |
| 2003/0199857 | A1 | 10/2003 | Eizenhofer |
| 2004/0249269 | A1* | 12/2004 | Shiono ................... A61B 8/08 |
| | | | 600/449 |
| 2004/0249271 | A1 | 12/2004 | Besson |
| 2006/0100552 | A1 | 5/2006 | Schultheiss |
| 2007/0142753 | A1 | 6/2007 | Warlick |
| 2009/0017107 | A1 | 1/2009 | Farber |
| 2012/0296240 | A1* | 11/2012 | Azhari .................... A61N 7/02 |
| | | | 606/1 |
| 2013/0103028 | A1* | 4/2013 | Tsoref ................ A61B 18/1492 |
| | | | 606/41 |
| 2013/0197404 | A1* | 8/2013 | Spector ............. A61B 17/2251 |
| | | | 601/15 |
| 2017/0196766 | A1 | 7/2017 | Spector |
| 2019/0209431 | A1* | 7/2019 | Warlick ............... A61H 39/007 |

OTHER PUBLICATIONS

Haddad, S., S. 0. Petenusci, J. A. Anselmo Franci, T. L. Lamana Carvalho. "Stimulation of prepubertal, pubertal and adult rat testis with low-instensity pulsed ultrasound." Archives Internationales de Physiologie, de Biochimie et de Biophysique. 1994. vol. 102, pp. 13-16. (Year: 1994).

Joelle Dupont, "Insulin signalling and glucose transport in the ovary and ovarian function during the ovarian cycle", 2016.

Anna Weihs, "Shock Wave treatment enhances cell proliferation and improves wound healing by ATP release-coupled extracellular signal-regulated kinase (ERK) activation", 2014.

Hellstrom, Wayne J. G., Mary Bernice Kaack, Richard M. Harrison, Durwood E. Neal JR., and Raju Thomas. "Absence of Long-Term Gonadotoxicity in Primates Receiving Extracorporeal Shock Wave Application". (1993) Journal of Endourology. vol. 17, No. 1. Retrieved from http://doi.org/10.1089/end.1993.7.17 (Year: 1993).

Lei et al., "Low-intensity Pulsed Ultrasound Improves Erectile Function in Streptozotocin-induced Type I Diabetic Rats". 2015. Urology 86 (6). (Year: 2015).

* cited by examiner

ACOUSTIC SHOCK WAVE TREATMENT AND DEVICES FOR APPENDAGES

FIELD OF THE INVENTION

The present invention relates to improved treatments of appendages for repairing or regenerating cells, tissues or vessels to overcome various degenerative conditions.

BACKGROUND OF THE INVENTION

The use of treating appendages such as hands, feet, the penis or scrotum using acoustic shock waves is known by the inventors of the present invention to treat various conditions such as poor circulation, arthritis in the hands or feet, erectile dysfunction in the penis and in the case of the scrotum increasing low testosterone levels. All of these appendages have a common feature of being relatively thin having less tissue to absorb emitted acoustic shock waves. In the case of hands, near the fingers and in feet near the toes. This result is particularly true in the waves passing through the tissue so quickly some if not most of the transmitted energy exits prior to being absorbed in the treated appendages. The present invention described in detail in this application greatly improves the absorption of the shock waves by redirecting the exiting waves reflecting them back into the treated appendage. In treating male infertility, this has provided a superior way to treat the penis.

Treating conditions of male infertility and impotency is extremely important for those affected by conditions such as Erectile Dysfunction.

In some cases, men take drugs to enhance their sexual performance and stamina. These medications, while beneficial, have some adverse consequences. The use of testosterone enhancing steroids for example can lead to serious complications.

In U.S. Pat. No. 7,601,127 B2, the inventor found that treating male genitalia including the penis with acoustic shock waves could overcome such conditions such as impotency, including erectile dysfunction.

The present invention has found a way to more effectively treat these conditions with faster and more reliable results by applying acoustic shock waves directly to the penis as discussed hereinafter.

Erectile Dysfunction (ED) is an ailment in which a male is unable to achieve or sustain an erection suitable for sexual intercourse. A number of factors are believed to play a role in or be directly responsible for ED, including obesity, blood pressure, chronic illnesses such as diabetes, poor blood flow to the penis, smoking tobacco, alcoholism, and side-effects of other medications.

Treatments for ED currently include cessation of potential causes such as smoking tobacco and consumption of alcohol, hormone (testosterone) replacement, surgery, and administration of pharmaceuticals such as vardenafil, tadalafil, and sildenafil. Some of these pharmaceuticals are controversial for their incompatibility with nitrate drugs, and for their unwanted side-effects, such as effects on vision (blurring, loss of vision) and priapism.

One objective of the present invention is to assist in regeneration of the male reproductive tissues and organs to correct at least partially degenerative conditions resulting from aging or disease. Another objective of the present invention is to stimulate the healing process of the male reproductive system after corrective surgery in cases where surgery is required to repair a defect in reproductive tissue or organs. Another objective is to stimulate tissue revascularization and blood flow effectively to improve either performance or sensitivity to sexual contact thereby enhancing sexual experience for a male. These and other objectives are achieved using the inventive technology described herein. The present invention provides new improved treatment methods and devices to accomplish these improvements as described hereinafter.

SUMMARY OF THE INVENTION

An improved method of treating an appendage of a patient using acoustic shock waves has the steps of: providing an appendage in need of an acoustic shock wave treatment; placing an acoustic shock wave applicator on a surface of the appendage; placing a gaseous filled membrane on an opposite surface of the appendage; activating an acoustic shock wave generator or source to emit acoustic shock waves from an acoustic shock wave applicator; and wherein the acoustic shock wave is transmitted from the acoustic shock wave applicator through the surface sending the emitted acoustic shock waves into the tissue of the appendage and exiting the opposite surface of the appendage to the gaseous filled membrane where a reflection of the acoustic shock wave occurs sending reflected acoustic shock waves back through the appendage.

The step of activating the acoustic shock wave generator or source emits low energy or unfocused acoustic shock waves. The acoustic shock waves are waves having amplitudes above 0.1 MPa and rise times of the amplitude are below 100 nano-seconds with a duration of a shock wave being below 3 micro-seconds for the positive part of a cycle and wherein the pressure pulses are an acoustic pulse which includes several cycles of positive and negative pressure with amplitudes of the positive part of such a cycle being above 0.1 MPa and the pressure pulse time duration is from below a microsecond to about a second, rise times of the positive part of the first pressure cycle is in the range of nano-seconds up to several milli-seconds.

The method of treating an appendage of a patient using acoustic shock waves further includes subjecting the appendage to the acoustic shock waves stimulating said appendage, the appendage is positioned within a path of the emitted shock waves stimulating a cellular response. The gaseous filled membrane has an internal chamber filled with air, nitrogen or other inert gas, the chamber having a thickness of at least 1 cm or more. The gaseous filled membrane has an elastomeric conformable exterior surface that conforms to the shape of the surface of the appendage when pressed against the appendage.

The method further has the step of applying an acoustic gel to the surfaces of the appendage and the acoustic shock wave applicator and the gaseous filled membrane to acoustically couple the surfaces to enhance transmission of the acoustic shock waves. The method further has the step of holding or pressing the applicator and the gaseous filled membrane firmly against opposing surfaces of the appendage to enhance the acoustic coupling.

In a preferred embodiment, the acoustic shock wave applicator is electrohydraulic and has a fluid filled flexible membrane. Other types of applicators including ballistic, piezoelectric, radial or spherical applicator devices can be used.

The gaseous filled membrane is one of a balloon, or a mitten or a glove. The glove or mitten has the gaseous filled membrane on a palm side of the mitten or glove, and the method further comprises the step of holding the balloon against the appendage or donning the mitten or glove and holding the appendage against the palm side to reflect or absorb the emitted shock waves. The membrane is configured to eliminate or at least greatly reduce shock waves from being transmitted to the hand of the person pressing the membrane against the appendage.

The appendage is of one of a hand, a foot, a penis, or a scrotum. The appendage in one treatment method is a penis of an adult post pubertal male and the penis exhibits erectile dysfunction. The emitted shock waves or pressure pulses are convergent, divergent, planar or near planar. The emitted shock waves or pressure pulses are convergent having one or more geometric focal volumes or points located at a distance X, X being defined as the distance from an exit window to the one or more focal volumes or points from the generator or source, the erect penis being positioned at the distance X or less than the distance X from the exit window source.

The method of treatment can further has the step of lowering the temperature of the appendage being treated to change tissue impedance to improve tissue stimulation.

DEFINITIONS

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

Cryotherapy, sometimes known as cold therapy, is the local or general use of low temperatures in medical therapy. When exposed to low temperatures, the blood vessels are narrowed and make less blood flow to the areas of swelling. Once outside the cryogenic chamber, the vessels expand, and an increased presence of anti-inflammatory proteins (IL-10) is established in the blood. Cryotherapy chamber involves exposing individuals to freezing dry air (below $-100°$ C.) for 2 to 4 minutes. One type of cryotherapy can be a WBC (whole body cryotherapy) chamber that is set at approximately $-230°$ F. for 2-4 minutes at a time to keep body temperature the same, since it's for such a short period of time, while bringing the skin temperature down to about $30°$ F.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"Erectile dysfunction (ED)" is an ailment in which a male is unable to achieve or sustain an erection suitable for sexual intercourse.

"extracorporeal" occurring or based outside the living body.

A "generalized paraboloid" according to the present invention is also a three-dimensional bowl. In two dimensions (in Cartesian coordinates, x and y) the formula $y^n=2px$ [with n being $\neq 2$, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p (-z,+z)), with z being a measure for the burn down of an electrode, and n, so that phenomena including, but not limited to, burn down of the tip of an electrode (-z,+z) and/or disturbances caused by diffraction at the aperture of the paraboloid are compensated for.

"impotence" an abnormal physical or psychological state of a male characterized by inability to copulate because of failure to have or maintain an erection-called also erectile dysfunction.

A "paraboloid" according to the present invention is a three-dimensional reflecting bowl. In two dimensions (in Cartesian coordinates, x and y) the formula $y^n=2px$, wherein p/2 is the distance of the focal point of the paraboloid from its apex, defines the paraboloid. Rotation of the two-dimensional figure defined by this formula around its longitudinal axis generates a de facto paraboloid.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milliseconds (ms). Very fast pressure pulses are called shock waves. Shock waves used in medical applications do have amplitudes above 0.1 MPa and rise times of the amplitude can be below 1000 ns, preferably at or below 100 ns. The duration of a shock wave is typically below 1-3 microseconds (µs) for the positive part of a cycle and typically above some micro-seconds for the negative part of a cycle.

"Shock Wave": As used herein is defined by Camilo Perez, Hong Chen, and Thomas J. Matula; Center for Industrial and Medical Ultrasound, Applied Physics Laboratory, University of Washington, 1013 NE 40th Street, Seattle, Washington 98105; Maria Karzova and Vera A. Khokhlovab; Department of Acoustics, Faculty of Physics, Moscow State University, Moscow 119991, Russia; (Received 9 Oct. 2012; revised 16 Apr. 2013; accepted 1 May 2013) in their publication, "Acoustic field characterization of the Duolith: Measurements and modeling of a clinical shock wave therapy device"; incorporated by reference herein in its entirety.

Wave energy or energy flux density: the measurement of energy flux density is defined as the energy directed toward the target or region being treated. This is not energy at the gap between electrodes, but rather the energy transmitted toward the patient's tissue through the skin. Important to distinguish that the energy levels discussed pertain to the energy delivered to the targeted tissues and not at the discharge point between the electrode tips. Spherical waves have a huge amount of energy produced between the tips to deliver adequate energy to the targeted tissues since they do not have the advantage of a lens.

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which.

DETAILED DESCRIPTION OF THE INVENTION

Figure 1:
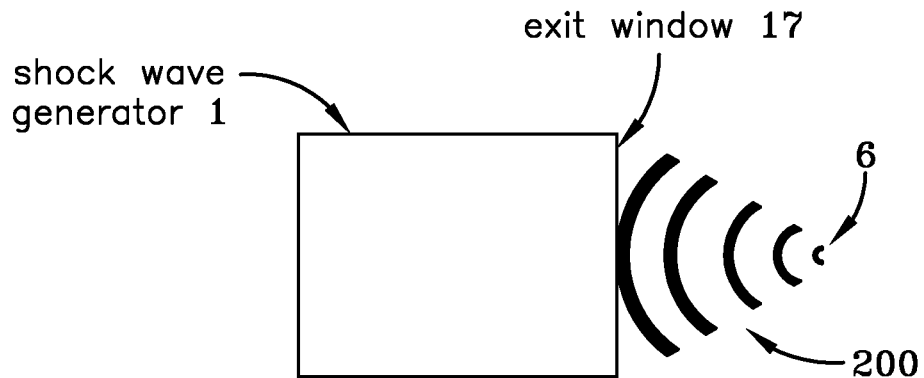
FIG. 1 is a simplified depiction of a pressure pulse/shock wave (PP/SW) generator with focusing wave characteristics.
Figure 2:
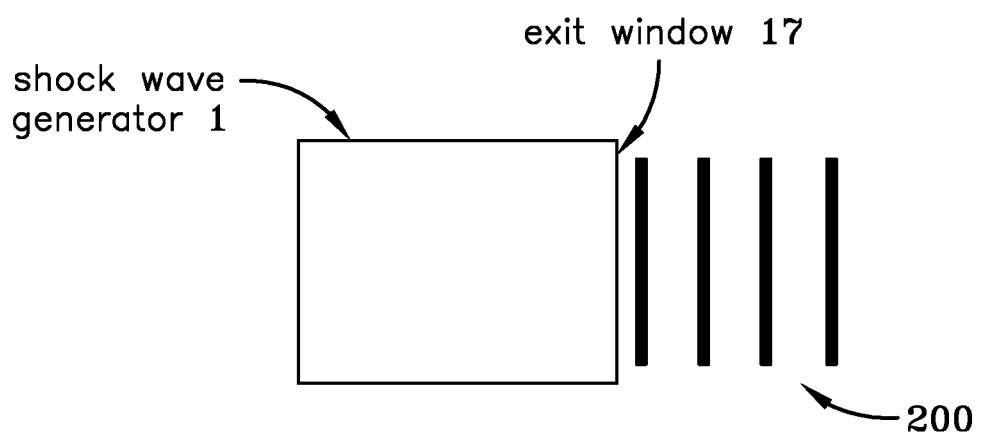
FIG. 2 is a simplified depiction of a pressure pulse/shock wave generator with plane wave characteristics.
Figure 3:
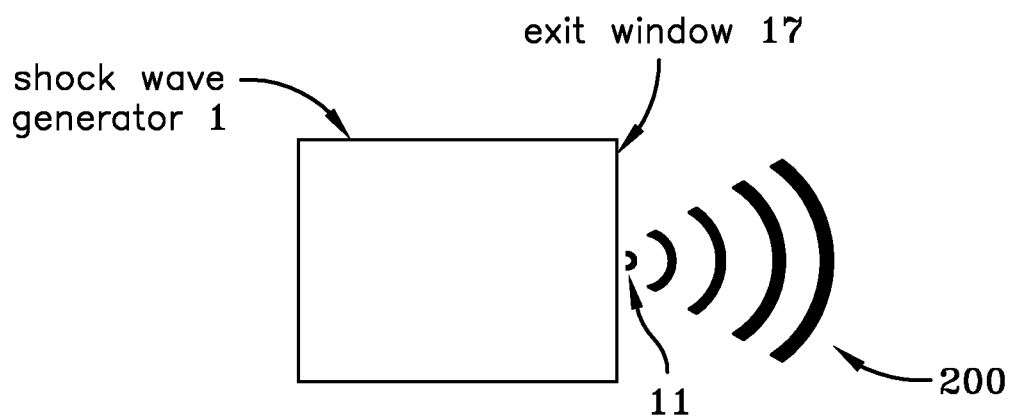
FIG. 3 is a simplified depiction of a pressure pulse/shock wave generator with divergent wave characteristics.

With reference to the figures, FIGS. 1-3 show various shock waves 200 being transmitted from a shock wave generator 1. FIG. 1 is a focused shock wave wherein the shock wave pattern emits from an exit window 17 and focuses to a point or localized area 6 as illustrated. The wave form 200 is considered a converging wave form. In FIG. 2, the shock wave emits from the exit window 17 in a planar fashion wherein the wave forms 200 are transmitted parallel to the exit window 17 and transmitted into the patient. In FIG. 3, the wave form 200 is emitted from the exit window 17 in such a fashion that the focal point is near the exit window 17 and the wave form 200 expands outwardly, this is considered a divergent wave form wherein the wave form expands as it leaves the exit window 17 in a diverging pattern.

Figure 4:
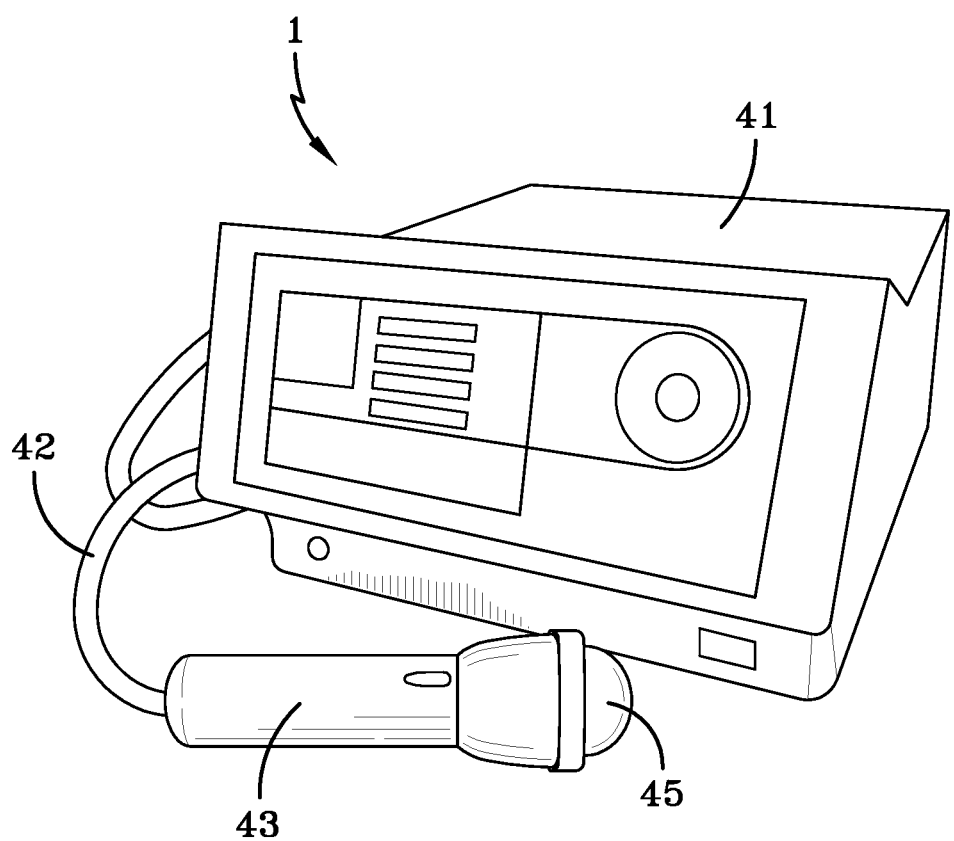
FIG. 4 is a perspective view of a shock wave generator device.

FIG. 4 shows an exemplary shock wave device generator or source 1 with a control and power supply 41 connected to a hand-held applicator shock wave head 43 via a flexible hose 42 with fluid conduits. The illustrated shock wave applicator 43 has a flexible membrane 45 at an end of the applicator 43 which transmits the acoustic waves when coupled to the external surface of tissue of an appendage by using a fluid or acoustic gel. As shown, this type of applicator 43 has a hydraulic spark generator using either focused or unfocused shock waves, preferably in a low energy level, less than the range of 0.01 mJ/mm$^2$ to 0.3 mJ/mm$^2$. The flexible hose 42 is connected to a fluid supply that fills the applicator 43 and expands the flexible membrane 45 when filled. Alternatively, a ballistic, piezoelectric or spherical acoustic shock wave device can be used to generate the desired waves. The fluid expands a flexible membrane 45 in such a fashion that the membrane 45 extends outwardly in a balloon shape fashion as illustrated in FIG. 4.

Figure 5:
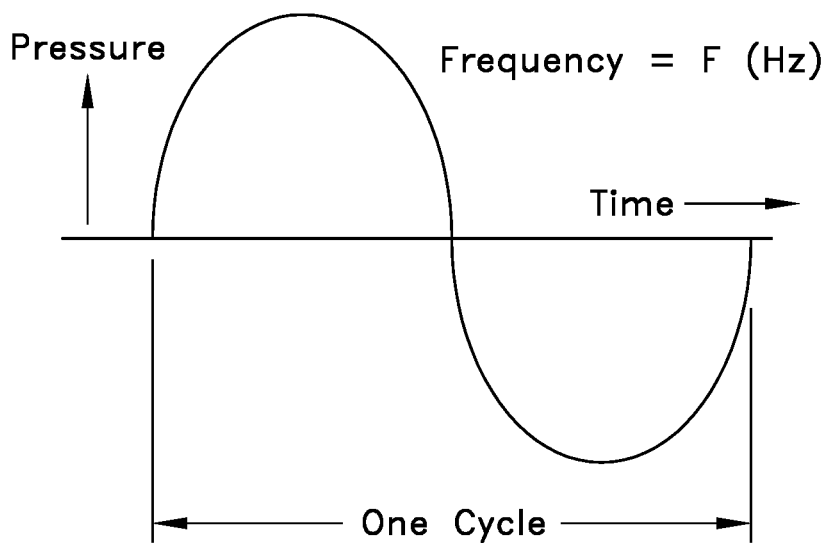
FIG. 5 is a graph showing an exemplary ultrasound wave pattern.
Figure 6:
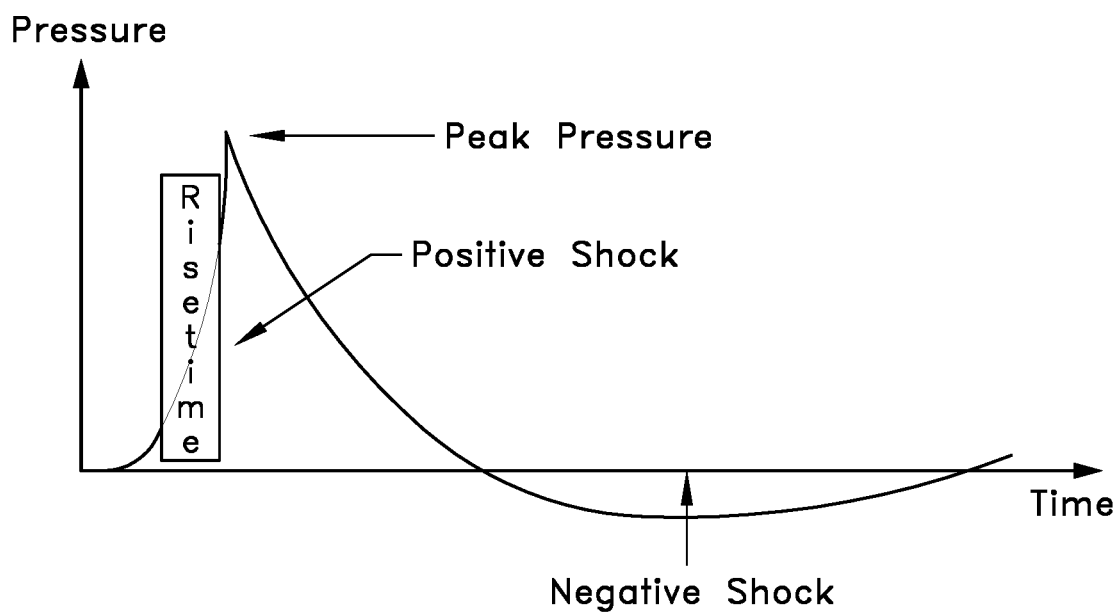
FIG. 6 is a graph of an exemplary acoustic shock wave pattern.

An important aspect of the present invention is that the pressure waves from the acoustic shock wave generator have an asymmetric type wave form with a very high peak pressure that occurs over a very short rise time. The positive shock is transmitted in a very quick fashion as defined which defines the features of an acoustic shock wave or pressure pulse. The negative portion of the wave is longer in duration and encompasses the rest of the wave form as shown in FIG. 6. This is unlike ultrasound wave forms which are symmetrical, sinusoidal in shape as illustrated in FIG. 5. The main difference between an acoustic shock wave and an ultrasound wave is that there is no heat generated in the asymmetric type acoustic shock wave whereas there is heat generation in the ultrasound wave. The ultrasound wave therefore is considered inferior for the purposes of erectile dysfunction or any other treatment for that matter compared to the use if the electrohydraulic acoustic shock waves emitted from the applicator 43. The applicator 43 as shown is electrohydraulic, but it could be ballistic, piezoelectric or any other form of applicator exhibiting the asymmetrical waves. The asymmetric acoustic wave pattern shown in FIG. 6 is contrasted to an ultrasonic wave pattern which is illustrated in FIG. 5. As shown, ultrasound waves are symmetrical having the positive rise time equal to the negative in a sinusoidal wave form. These ultrasound waves generate heat in the tissue and are accordingly believed not suitable for use on tissue requiring a cellular stimulation to achieve the desired goals of the treatment method.

Figure 7:
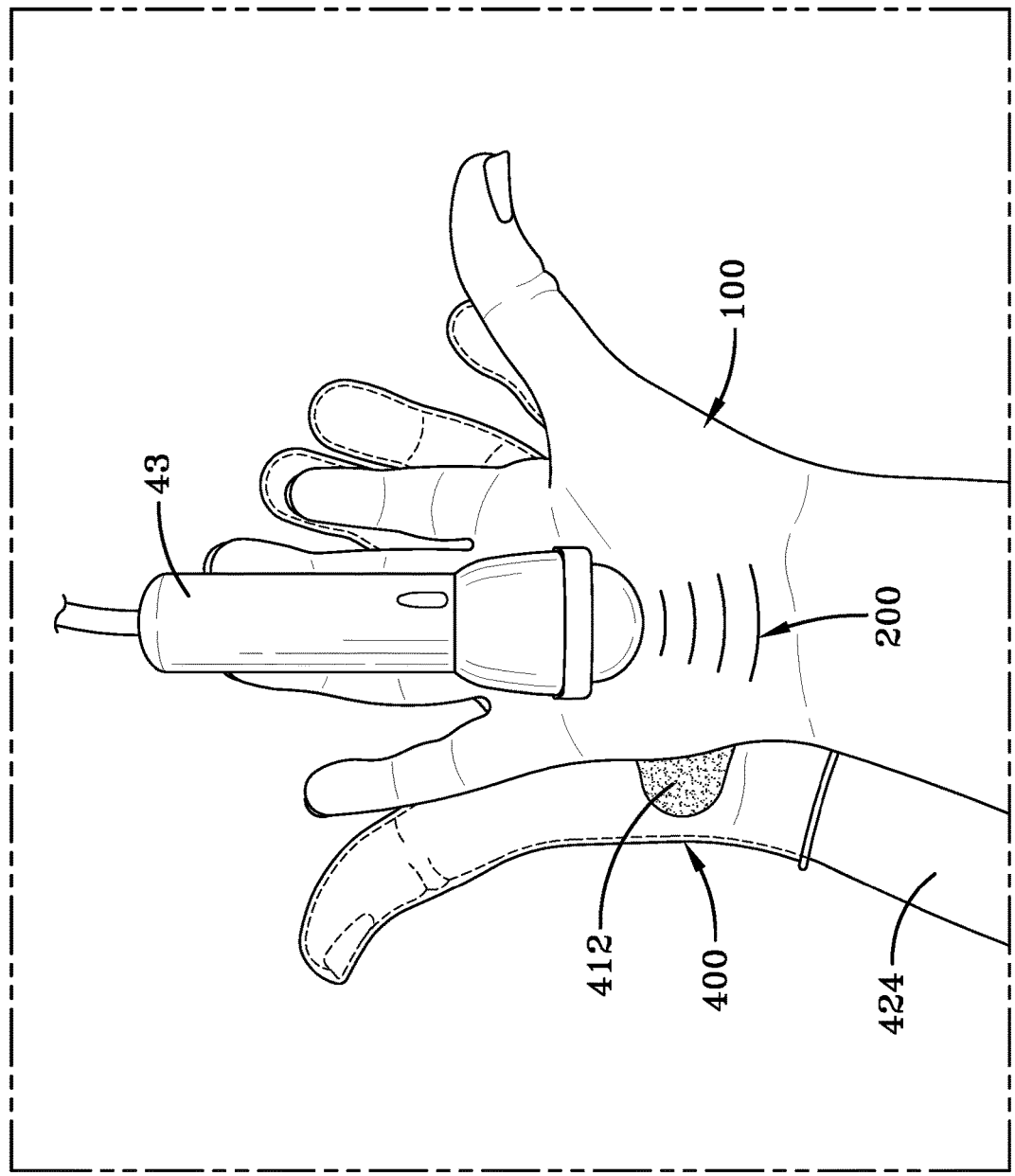
FIG. 7 is a hand being treated.
Figure 8:
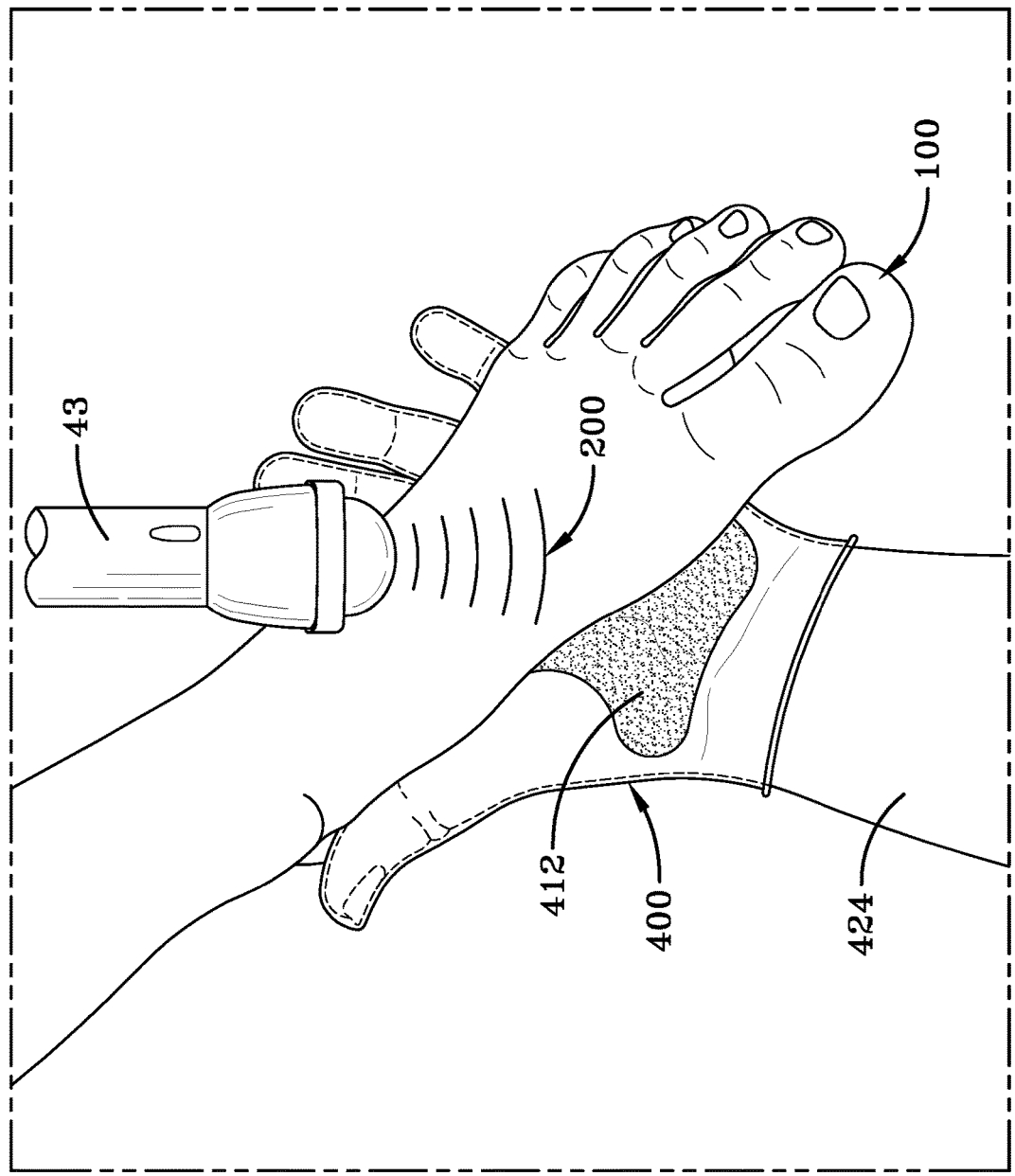
FIG. 8 is a foot being treated.
Figure 9:
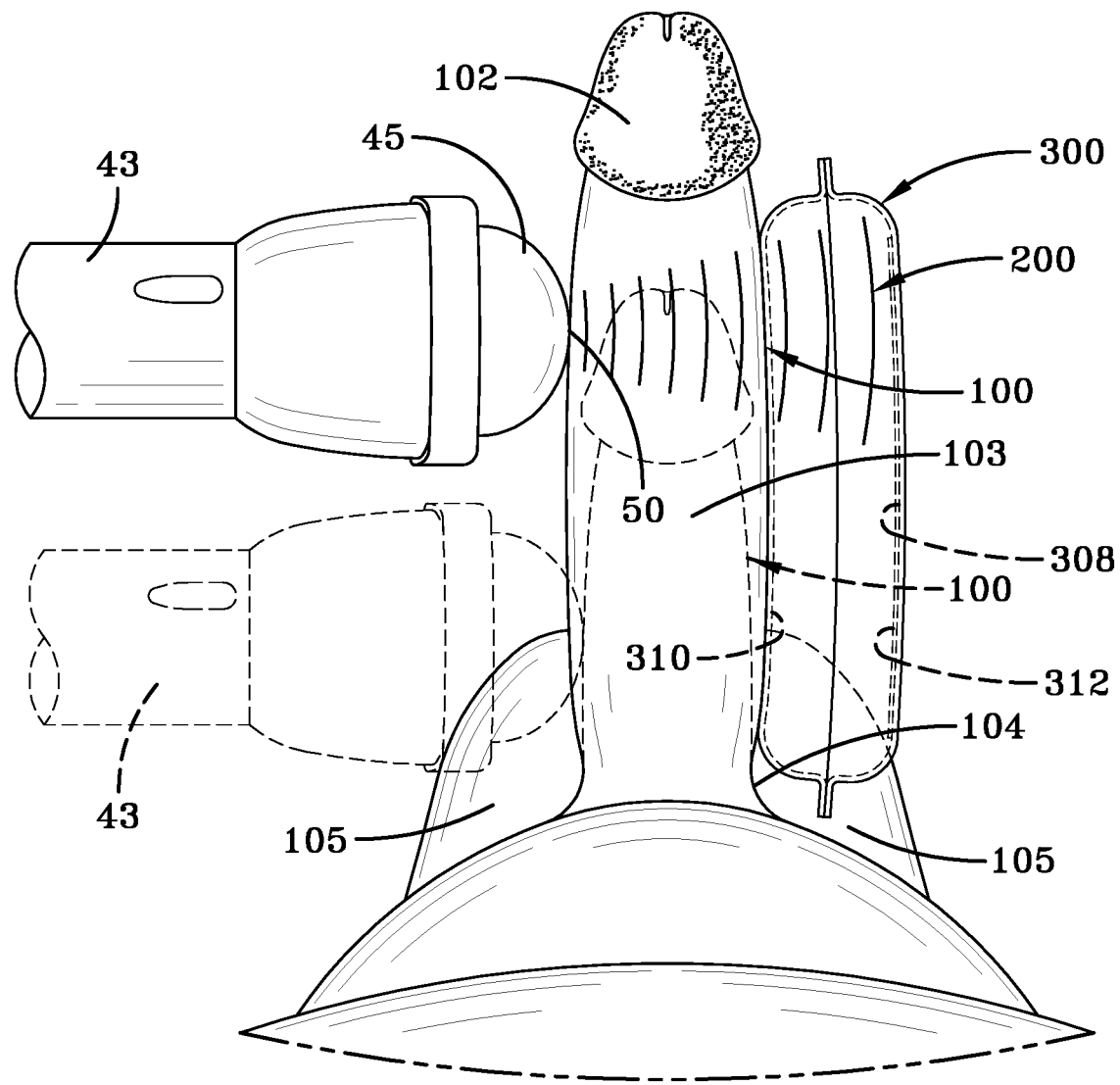
FIG. 9 is a view of the penis being treated with a balloon conformed on one side.

With reference to FIGS. 7, 8 and 9, an improved method treating appendages has been discovered wherein the appendage can be one of a hand as illustrated in FIG. 7, a foot illustrated in FIG. 8, or a penis illustrated in FIG. 9. In each of these embodiments, the shock wave applicator 43 as previously discussed is positioned on one side of the appendage 100 whether it be the hand, foot or the penis. On the opposite side of the applicator contacting surface is preferably a gaseous filled membrane 300 which is placed against the skin surface of the appendage 100 as illustrated in FIG. 9. Preferably, the gas filled membrane 300 has an exterior surface that has been treated with a coupling gel 50, like ultrasound gel to ensure the shock wave transmissions 200 transmitted from the applicator 43 through the appendage 100 that exit the appendage impact the flexible gaseous filled membrane 300 that conforms to and is coupled to the appendage 100 that it is pressed against. In an alternative embodiment, the gaseous filled membrane 300 can have a reflective interior appendage side surface 310 and a reflective interior opposite side surface 308, 312 of the gaseous filled membrane 300.

Figure 10:
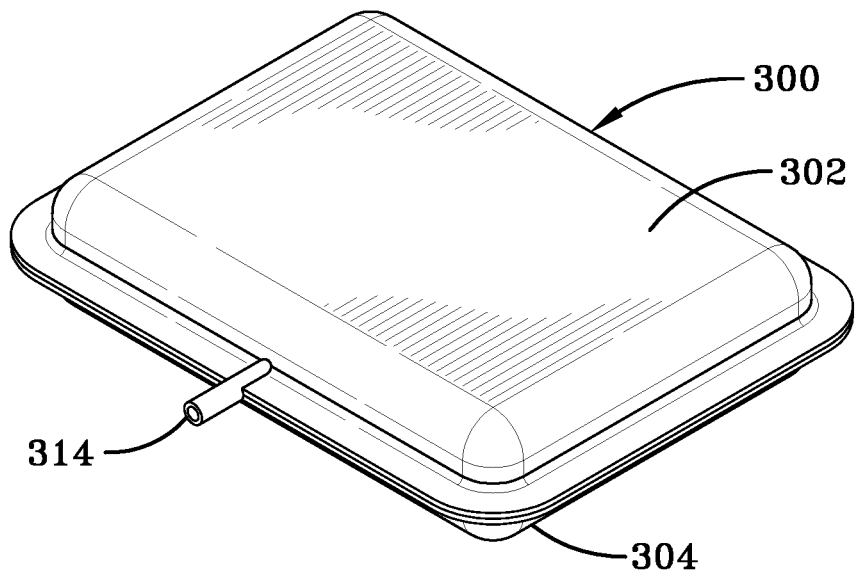
FIG. 10 is a view of the gaseous filled membrane as a balloon.
Figure 11:
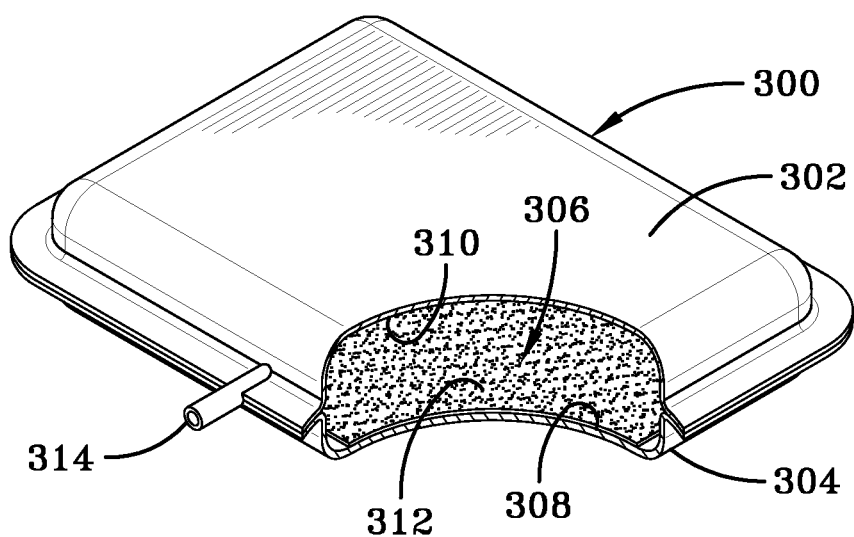
FIG. 11 is a view taken from FIG. 10.

FIGS. 10 and 11 illustrate an exemplary gaseous filled membrane in the form of a balloon or bag 300. The balloon or bag 300 has exterior surfaces 302 and 304. The balloon or bag also has interior surfaces 310, 308 and 312 that can have a reflective coating to better reflect and redirect the acoustic shock waves 200. The gaseous filled membrane can contain various types of fluid 306.

Figure 14:
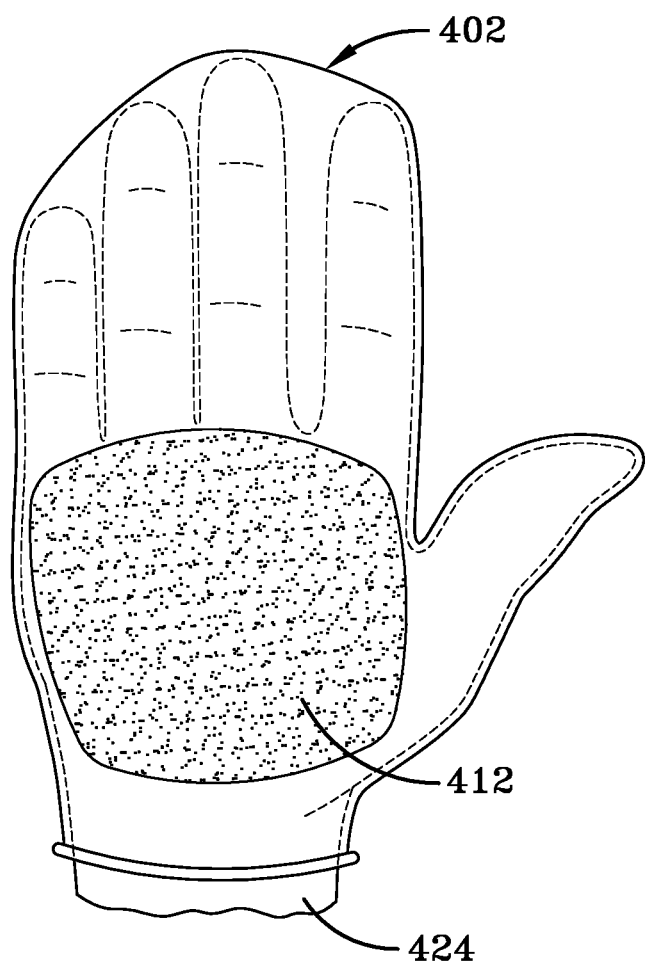
FIG. 14 is a view of a mitten with a gaseous filled membrane on the palm side of the mitten.

In a preferred embodiment, the gaseous filled membrane is pressed against the appendage using the technician's hand. In one embodiment, a glove 400 or mitten 402 is provided that has the gaseous filled membrane 412 on the palm side of the glove 400 or mitten 4002 in such a way that the gaseous filled membrane 412 is in direct contact with the surface of the appendage 100 being held. An exemplary glove 400 and mitten 402 are illustrated in FIGS. 12 and 14 respectively.

Figure 12:
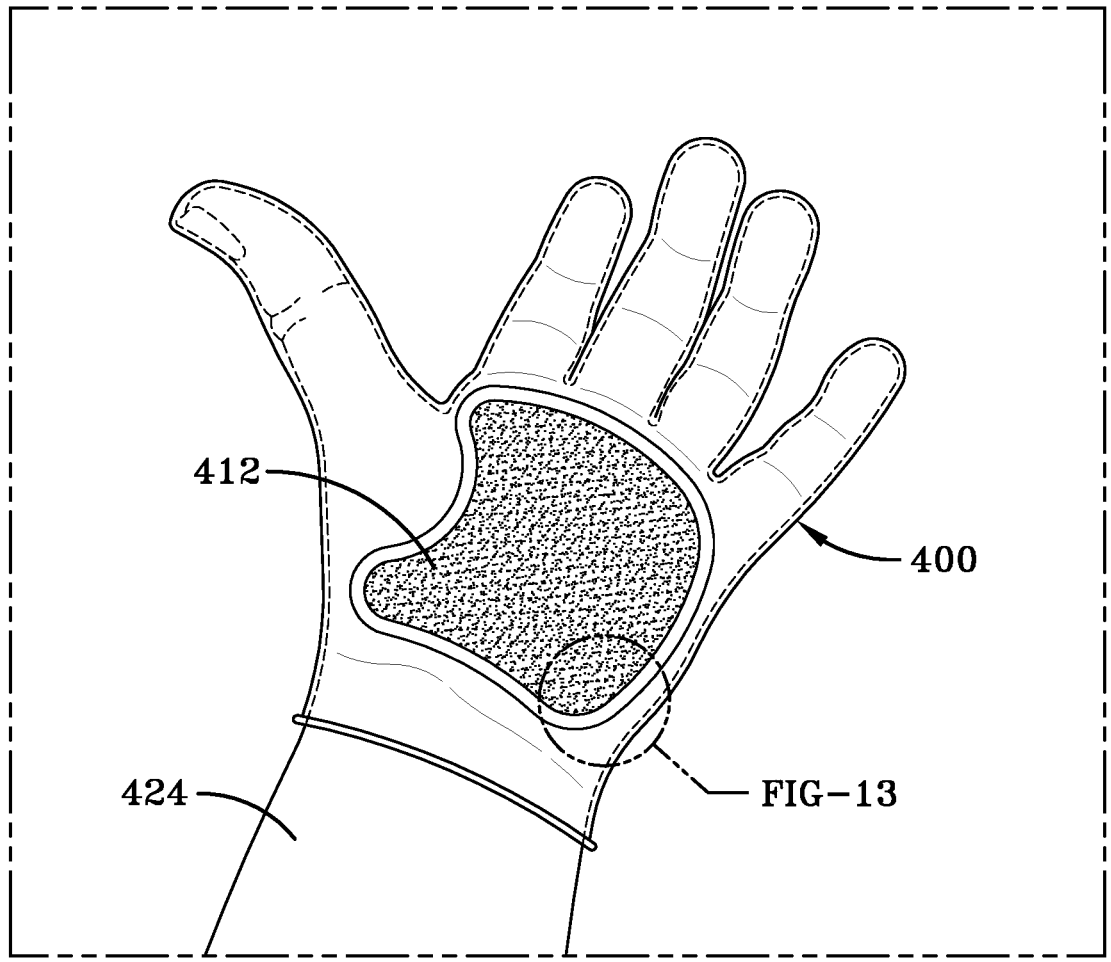
FIG. 12 is a view of a glove with a gaseous filled membrane on the palm side of the glove.
Figure 13:
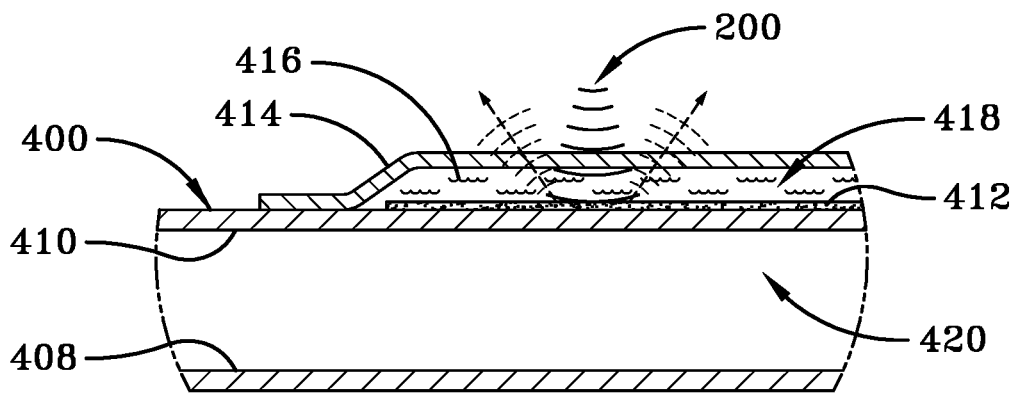
FIG. 13 is a cross section taken from FIG. 12.

FIG. 13 is a cross section of a portion of the glove 400 taken from FIG. 12 showing the gaseous filled membrane 412 on the palm portion filled with a fluid 416. The glove 400 has interior surfaces 408 and 410 with the area 420 for the technician's 424 hand. The shock waves 200 are shown being reflected from the gaseous filled membrane 412 that has an internal area 418 filled with a fluid 416. Surface 414 that contacts the appendage 100 to be treated is shown opposite the technician hand receiving area 420.

As shown in FIG. 7, when the shock wave applicator 43 is activated, the appendage 100 shown as a hand has the acoustic shock waves 200 being transmitted through the tissue and areas of the hand near the fingers. In FIG. 8, the appendage 100 shown as a foot is being treated with the shock wave applicator 43. In areas where the fingers or toes are, the appendage is quite thin and the shock wave transmissions 200, even at low energy, are easily transmitted through the appendage 100 and exit out the exterior side. The technician, when holding the appendage 100 firmly against the applicator 43 ensures that the shock waves 200 are transmitted efficiently from the applicator head through the tissue. Unfortunately, the exiting shock waves 200 are then transmitted into the hand of the technician 424. This can be relatively uncomfortable for the technician, but more importantly after treating many patients, the technician 424 is basically treating his or her own hand with acoustic shock waves 200 that have been transmitted through the appendage 100.

In order to facilitate the treatment and allow for a firm pressure to be applied to the appendage 100 whether it be a penis or a hand or a foot, the technician 424 should firmly press the appendage 100 against the applicator 43. If a mitten 402 or glove 400 with a flexible membrane or a gaseous filled balloon membrane 412 is used, the technician 424 can apply a force against the gaseous filled membrane 412 in such a fashion that it conforms directly against the surface of the skin of the appendage 100 in such a fashion that the exiting shock waves 200 are transmitted towards the gaseous filled membrane 412.

It was discovered that the shock waves 200 upon exiting and impinging the membrane 412 or balloon 300, were redirected and reflected back into the tissue of the appendage 100 being treated. This reflection back of the exiting acoustic shock waves means that the shock waves can be provided in such a fashion that they initially impinge the tissue on the applicator side being directed in one direction and thereafter are reflected back into the appendage 100 as the reflected shock waves enter the opposite side of the appendage where the gaseous filled membrane 412, 300 is located and are directed back into the tissue of the appendage 100. This increases the amount of shock wave exposure to all the cells within the appendage 100. As can be appreciated, this actually has the effect of increasing the stimulating response of the acoustic shock waves 200 being delivered to the appendage 100. The inventors found that this is not an insignificant amount of reflection of acoustic shock waves, up to half of the acoustic wave stimulation effect can be achieved by the reflected waves. While this may be an interesting phenomenon, what is very important is that as a result of this it is believed that the number of shock waves required to treat a particular appendage can be dramatically reduced. When these shock waves are reduced, the number of times that the electrode must fire to emit the shock waves can also be reduced. This is significant in that as the electrodes are fired, the electrode tips tend to wear, as they wear, they lose efficiency to a point that after a number of shock waves have been transmitted, the electrode must be replaced. To do this, the applicator is sent back to the manufacturer to have new electrodes installed. This refurbishment can be expensive and causes a cost to be incurred by the operator or owner of the equipment. This cost can be greatly reduced if the use of the reflective gaseous filled membrane is applied to the appendages because the number of shock waves required can be reduced due to this reflection phenomenon of the exiting shock waves being transmitted back into the tissue being treated.

As shown in FIG. 14, in one embodiment, the gaseous filled membrane 412 is placed on the palm side of a mitten 402. In this fashion, the wearer 424 of the mitten 42 can cradle the appendage 100 to apply the appropriate pressure as disclosed. In this fashion, the membrane 412 can be rather simply constructed with a single chamber. Alternatively, as shown in FIG. 7, if desired, the gaseous membrane 412 can be on a glove 400 with fingers, preferably the glove 400 has the palm side having the gaseous membrane 412 inserted and the gaseous membrane extends to each of the fingers including the palm so that as the technician 424 is holding the appendage 100, the transmitted shock waves 200 are absorbed and reflected back into the tissue or appendage 100 being treated. In this way, the energy that would otherwise be impinging on the technician's hand is virtually eliminated in a way such that the technician 424 can feel comfortable in holding the appendage 100 without experiencing the sensation of treating his or her own hand with the exiting shock waves 200.

It is further believed that these exiting shock waves 200 when reflected have a reduced tensile component in the shock wave itself in such a fashion that the reflected shock wave transmits a compressive force back into the tissue to stimulate the cells with a reduced tensile component that can improve the effectiveness of the acoustic shock waves.

An important aspect of the present invention is that, as illustrated in FIG. 9, the shock wave applicator 43 when applied to a penis 100 for treating erectile dysfunction is generally held in one hand by the technician and the other hand holds a gaseous membrane in the form of a balloon 300 that extends along the shaft of the penis 100. It has been determined that during these treatments, the acoustic shock waves 200 on a flaccid penis 100, that is a non-erect penis, is such that the wave transmission extends beyond the diameter DS of the non-erect penis 100. In fact, the non-erect penis 100, shown in dashed lines for comparison, has a diameter DS of approximately greater than 2 cm typically. Whereas the acoustic shock wave applicator 43 membrane 45 and exit window that emits most of the energy is approximately 5 cm diameter. When this occurs, the technician who supports the shaft 103 of the penis 100 has a hand holding the penis lying along the shaft 103 to support the penis 100 and as the shock wave transmission is transmitted through the flaccid penis 100 the energy gets transmitted to the technician and the technician is actually treating his or her hand with shock waves due to the fact that the non-erect penis is sufficiently small in diameter that it allows for energy to be transmitted past and through the soft penis 100. After having been treating penises of this type, it was noticed that if a penis was made to have an erection, the shaft 103 of the penis increases by approximately one third to greater than 3 cm, typically about 5 cm which is approximately the size of the applicator head for the emitted energy pulse being transmitted. In this case, the technician is holding the applicator 43 in one hand and the other hand is extending along the shaft of the penis, the energy transmission is primarily absorbed through the erect penis 100 due to the increased size/diameter DE.

This erection of the penis 100 not only increases the diameter DE which approximates the size of the wave form 200 being transmitted but also increases the length from LS for the non-erect penis to LE for the erect penis length. This enables the device to be able to transmit as one can appreciate when the membrane of the applicator 43 is pressed against the erect penis 100, the entire membrane can be moved along the shaft 103 from the head 102 to the base 104 near the testicles or scrotum 105 to treat the penis 100 for erectile dysfunction. As the technician rotates the applicator 43 about the shaft 103 of the penis 100, it can be moved diametrically around the shaft of the penis as well as along the length LE of the penis 100 ensuring the entire length of the penis is being effectively treated with acoustic shock waves 200.

These acoustic shock waves create increased vascularization and blood flow. Since the patients being treated are afflicted with erectile dysfunction, it is very difficult to maintain an erection. Accordingly, the patient could be given a simple treatment of taking a medication that will assist in maintaining an erection for a period of time or preferably is given an injection with a chemical that will artificially create the erection.

A chemical or artificial erection involves injection of medications such as alprostadil, a formulation of prostaglandin E, available under various trade names. For example, one medication is a mixture of prostaglandin, phentolamine, and papaverine into the base of the penis causing an erection.

In the present invention, it was discovered that the emitted shock waves in either the flaccid or the erect penis passed through the penis into the gloved hand of the technician. This was not terribly detrimental, but as one of ordinary skill in the art can appreciate having the technician's hand exposed to such transmitted waves was not desirable. To overcome this occurrence, the inventors discovered that a gas filled membrane in the shape of a balloon could be held by the technician against the surface of an appendage, like the penis, on a side opposite that onto which the applicator is held and the exiting shock waves would be absorbed in the gas filled membrane eliminating the technician's hand from experiencing the sensation of feeling the shock waves. Unexpectedly, a portion of the exiting shock waves upon impinging the gaseous filled membrane were reflected back into the appendage. These reflected waves were reduced in energy, but still have levels of energy that stimulated a beneficial cellular stimulation in the appendage. These reflected waves had little or no tensile forces which actually is believed beneficial and in the case of low energy acoustic shock waves, there is little or no cavitation created which is evidenced by a lack of bruising or hematomas at the surface of the appendage meaning no cellular membrane ruptures are exhibited.

The inventors found air reflects shockwaves and placing an air bag in an exit path on skin of the appendage causes the acoustic waves to reflect back creating secondary waves with no tensile wave component.

Unfocused low energy acoustic shock waves reflected by a parabolic applicator creates a linear beam of unfocused energy, compression waves travel through tissue. The amplitude and intensity decrease with distance attenuation due to: Acoustic energy conversion is reduced by tissue absorption while redirection of energy via scatter, reflection, refraction, diffraction, divergence, Energy absorbed by penile tissues allows microtrauma which leads to neovascularization, tissue regeneration, reduction of inflammation stem cell activation. At the tissue interface, energy reflection vs transmission depends on difference in acoustic impedance between tissues. Small impedance mismatch means most energy transmitted with little reflected/refracted/scattered. Large impedance mismatch has the most energy reflected/refracted/scattered with little transmitted. Very small reflectors like RBCs, red blood cells, also produce scattering—'Rayleigh scatterers". This led the inventors to hypothesize that erect penile tissue energy absorption is much greater than flaccid penile tissue absorption due to increased impedance mismatch at blood-tissue interface of erect penis, increased scatter/refraction/diffraction due to more RBC/Rayleigh scatterers, larger erect penis diameter brings focal into tissue rather than outside penis, and acoustic waves propagate inside erect tissue instead of quickly through flaccid tissue.

The increased size of the erect penis lacunar spaces increases acoustic impedance mismatching. This fact when combined with a gaseous membrane added the reflection of shock waves to enhance cellular stimulation.

In the extracorporeal shock wave or pressure pulse method of treating tissue, the administered shock waves or pressure pulses are directed to a treatment location or target site on the tissue. As used herein, "near" recognizes that the emitted shock waves or pressure pulses are transmitted through the tissue, preferably at or in close proximity to the treatment location or site.

Assuming the target area is within a projected area of the wave transmission, a single transmission dosage of wave energy may be used. The transmission dosage can be from a few seconds to 20 minutes or more dependent on the condition. Preferably the waves are generated from an unfocused or focused source. The unfocused waves can be divergent or near planar and having a low-pressure amplitude and density in the range of 0.00001 mJ/mm$^2$ to 1.0 mJ/mm$^2$ or less, most typically below 0.2 mJ/mm$^2$. These are typically generated by spherical or radial wave generators, ballistic or electrohydraulic wave or piezoelectric shock wave generators. The focused source can use a focused beam of waves or can optionally use a diffusing lens or have a far-sight focus to minimize if not eliminate having the localized focus zone within the tissue. Preferably the focused shock waves are used at a similarly effective low energy transmission or alternatively can be at higher energy but wherein the tissue target site is disposed pre-convergence inward of the geometric focal point of the emitted wave transmission. Understanding the higher the energy used, the more sensation of bruising the tissue. In these cases, cavitation can and often does occur as well as bruising and come cell damage. This is preferably and easily avoidable by employing the gaseous filled membrane as previously discussed.

These shock wave energy transmissions are effective in stimulating a cellular response and in some cases, such as unfocused low energy, and even low energy focused emissions can be accomplished without creating the localized hemorrhaging caused by rupturing cavitation bubbles in the tissue of the target site. This effectively ensures the tissue does not have to experience the sensation of cellular damage so common in the higher energy focused wave forms having a focal point at or within the targeted treatment site. Higher energy acoustic shock waves or pressure pulses including focused waves can be used, but with care to avoid such damage.

The target site may be such that the tissue or the generating source must be reoriented relative to the site and a second, third or more treatment dosage can be administered. At a low energy, the common problem of localized hemorrhaging is reduced making it more practical to administer multiple dosages of waves from various orientations to further optimize the treatment and cellular stimulation of the target site. Alternatively, focused high energy multiple treatments can be equally effective, but with some risk to tissue bruising. The use of low energy focused or un-focused waves at the target site enables multiple sequential treatments. Alternatively, the wave source generators may be deployed in an array wherein the subject tissue is effectively enveloped or surrounded by a plurality of low energy wave source generators which can be simultaneously bombarding the target site from multiple directions. Such arrays include linear type devices.

The goal in such treatments is to provide 100 to 3000 acoustic shock waves or pressure pulses. Typically, at a voltage of 14 kV to 28 kV across a spark gap generator in a single treatment preferably or one or more adjuvant treatments by targeting the site directly by impinging the emitted waves toward the male penis.

The present method does not rely on precise site location per se. The physician's general understanding of the anatomy of the penile tissue should be sufficient to locate a desirable direct path or to the target site to attack the condition being treated. The treated area can withstand a far greater number of shock waves based on the selected energy level being emitted. For example, at very low energy levels the stimulation exposure can be provided over prolonged periods as much as 20 minutes if so desired. At higher energy levels the treatment duration can be shortened to less than a minute, less than a second if so desired. The selected treatment dosage can include the avoidance or minimization of cell hemorrhaging and other kinds of damage to the cells or tissue while still providing a stimulating cellular release activation of upregulation of the antimicrobial peptide LL37, a protein that can bind with RNA to destroy any infections, and also VEGF and other growth factors and can also be used to modulate and regulate spermal secretions from the specific targeted gland as in the testicles or penis by emitting waves to a desired direct path.

The underlying principle of these sound wave therapy methods is to stimulate the penile tissue. This is accomplished by deploying shock waves to stimulate strong cells in the tissue to activate a variety of responses, more particularly those that reduce inflammation and stop any infections. The sound waves including acoustic shock waves or pressure pulses transmit or trigger what appears to be a cellular communication throughout the entire anatomical structure of the penile tissue, this activates a generalized cellular response at the treatment or target site, in particular, but more interestingly a systemic response in areas more removed from the wave form pattern. This is believed to be one of the reasons molecular stimulation can be conducted at threshold energies heretofore believed to be well below those commonly accepted as required. Accordingly, not only can the energy intensity be reduced but also the number of applied shock wave impulses can be lowered from several thousand to as few as one or more pulses and still yield a beneficial stimulating response if desired.

The biological model motivated the design of sources with low pressure amplitudes and energy densities. First: spherical waves generated between two tips of an electrode; and second: nearly even waves generated by generated by generalized parabolic reflectors. Third: divergent shock front characteristics are generated by an ellipsoid. Unfocused sources are preferably designed for extended two dimensional areas/volumes like skin. The unfocused sources can provide a divergent wave pattern or a nearly planar wave pattern and can be used in isolation or in combination with focused wave patterns yielding to an improved therapeutic treatment capability that is non-invasive with few if any disadvantageous contraindications. Alternatively, a focused wave emitting treatment may be used wherein the focal point extends to the target site. In any event, the beam of acoustic waves transmitted needs to project in a large enough zone or area to stimulate or modulate the cells in the erect penis.

In one embodiment, the method of treatment has the steps of, generating either focused shock waves or unfocused shock waves, of directing these shock waves to the treatment site; and applying a sufficient number of these shock waves to induce activation of one or more growth factor or antimicrobial peptides like LL37, thereby inducing or accelerating a modulated adjustment to induce the host cells of the penis to attack any infection or disease. In this case, preferably to overcome ED.

The shock waves can be of a low peak pressure amplitude and density. Typically, the energy density values range as low as 0.000001 mJ/mm$^2$ and having a high end energy density of below 1.0 mJ/mm$^2$, preferably 0.40 mJ/mm$^2$ or less, more preferably 0.20 mJ/mm$^2$ or less. The peak pressure amplitude of the positive part of the cycle should be above 1.0 and its duration is below 1-3 microseconds.

The treatment depth can vary from the surface to the full depth of the penile tissue and the treatment site can be defined by a much larger treatment area. The above methodology is particularly well suited for surface as well as sub-surface soft tissue treatments in penile organs or tissue.

An exemplary treatment protocol could have emitted shock waves in a broad range of 0.01 mJ/mm$^2$ to 3.0 mJ/mm$^2$ and 200-2500 pulses per treatment with a treatment schedule of 1-3 treatments being repeated over several weeks.

In the shock wave method of treating the tissue of a patient diagnosed with infertility or impotence requires the patient to be positioned in a convenient orientation to permit the source of the emitted waves to most directly send the waves to the target site to initiate shock wave stimulation of the target area with minimal, preferably no obstructing features in the path of the emitting source or lens. Assuming the target area is within a projected area of the wave transmission, a single transmission dosage of wave energy may be used. The transmission dosage can be from a few seconds to 20 minutes or more dependent on the condition. Preferably the waves are generated from an unfocused or focused source. The unfocused waves can be divergent, planar or near planar and having a low pressure amplitude and density in the range of 0.00001 mJ/mm$^2$ to 1.0 mJ/mm$^2$ or less, most typically below 0.2 mJ/mm$^2$. The focused source preferably can use a diffusing lens or have a far-sight focus to minimize if not eliminate having the localized focus point within the tissue. Preferably the focused shock waves are used at a similarly effective low energy transmission or alternatively can be at higher energy but wherein the tissue target site is disposed pre-convergence inward of the geometric focal point of the emitted wave transmission.

These shock wave energy transmissions are effective in stimulating a cellular response and can be accomplished without creating the cavitation bubbles in the tissue of the target site. This effectively insures the penile tissue or organ does not have to experience the sensation of hemorrhaging so common in the higher energy focused wave forms having a focal point at or within the targeted treatment site.

Due to the wide range of beneficial treatments available it is believed preferable that the optimal use of one or more wave generators or sources should be selected on the basis of the specific application. Wherein relatively small target sites may involve a single wave generator placed on an adjustable manipulator arm. A key advantage of the present inventive methodology is that it is complimentary to conventional medical procedures. In the case of any operative surgical procedure the surgical area of the patient can be bombarded with these low energy waves to stimulate cellular release of healing agents and growth factors. This will dramatically reduce the healing process time. Most preferably such patients may be provided more than one such treatment with an intervening dwell time for cellular relaxation prior to secondary and tertiary post operative treatments.

Cryotherapy can be used to enhance shock wave therapy. Lowering the temperature of the tissue being treated changes the tissue impedance improving performance or cell stimulation. The shock wave therapy can occur at the same time as or immediately after the cryotherapy.

The underlying principle of these shock wave therapy methods is to stimulate the body's own natural healing capability. This is accomplished by deploying shock waves to stimulate strong cells in the penile tissue to activate a variety of responses. The acoustic shock waves transmit or trigger what appears to be a cellular communication throughout the entire anatomical structure, this activates a generalized cellular response at the treatment site, in particular, but more interestingly a systemic response in areas more removed from the wave form pattern. This is believed to be one of the reasons molecular stimulation can be conducted at threshold energies heretofore believed to be well below those commonly accepted as required. Accordingly, not only can the energy intensity be reduced but also the number of applied shock wave impulses can be lowered from several thousand to as few as one or more pulses and still yield a beneficial stimulating response.

The use of shock waves as described above appears to involve factors such as thermal heating, light emission, electromagnetic field exposure, chemical releases in the cells as well as a microbiological response within the cells. Which combination of these factors plays a role in stimulating healing is not yet resolved. However, there appears to be a commonality in the fact that growth factors are released which applicants find indicative that otherwise dormant cells within the tissue appear to be activated which leads to the remarkable ability of the targeted penile tissue to generate new growth or to regenerate weakened vascular networks in for example the reproductive system. This finding leads to a complimentary use of shock wave therapy in combination with stem cell therapies that effectively activate or trigger stem cells to more rapidly replicate enhancing the ability to harvest and culture more viable cells from the placenta, a nutrient culture of said stem cells, or other sources. The ability to stimulate stem cells can occur within the patient's own body activating the naturally occurring stem cells or stem cells that have been introduced to the patient as part of a treatment beneficially utilizing stem cells. This is a significant clinical value in its own right and is critical in attempts to overcome conditions of infertility.

The use of shock wave therapy requires a fundamental understanding of focused and unfocused shock waves, coupled with a more accurate biological or molecular model.

Focused shock waves are focused using ellipsoidal reflectors in electromechanical sources from a cylindrical surface or by the use of concave or convex lenses. Piezoelectric sources often use spherical surfaces to emit acoustic pressure waves which are self focused and have also been used in spherical electromagnetic devices.

The biological model proposed by Wolfgang Schaden provides a whole array of clinically significant uses of shock wave therapy.

Accepting the biological model as promoted by W. Schaden, the peak pressure and the energy density of the shock waves can be lowered dramatically. Activation of the body's healing mechanisms will be seen by in growth of new blood vessels and the release of growth factors.

The biological model motivated the design of sources with low pressure amplitudes and energy densities. First: spherical waves generated between two tips of an electrode; and second: nearly even waves generated by generalized parabolic reflectors. Third: divergent shock front characteristics are generated by an ellipsoid behind F2. Unfocused sources are preferably designed for extended two dimensional areas/volumes like skin. The unfocused sources can provide a divergent wave pattern a planar or a nearly planar wave pattern and can be used in isolation or in combination with focused wave patterns yielding to an improved therapeutic treatment capability that is non-invasive with few if any disadvantageous contraindications. Alternatively, a focused wave emitting treatment may be used wherein the focal point extends preferably beyond the target treatment site, potentially external to the patient. This results in the reduction of or elimination of a localized intensity zone with associated noticeable pain effect while providing a wide or enlarged treatment volume at a variety of depths more closely associated with high energy focused wave treatment. The utilization of a diffuser type lens or a shifted far-sighted focal point for the ellipsoidal reflector enables the spreading of the wave energy to effectively create a convergent but off target focal point. This insures less tissue trauma while insuring cellular stimulation to enhance the healing process and to effectively remodel the reproductive tissues or organs of the patient.

This method of treatment has the steps of, locating a treatment site, generating either convergent diffused or far-sighted focused shock waves or unfocused shock waves, of directing these shock waves to the treatment site; and applying a sufficient number of these shock waves to induce activation of one or more growth factors thereby inducing or accelerating healing and tissue and organ remodeling or repair.

The unfocused shock waves can be of a divergent wave pattern, planar or near planar pattern preferably of a low peak pressure amplitude and density. Typically, the energy density values range as low as 0.000001 $mJ/mm^2$ and having a high end energy density of below 1.0 $mJ/mm^2$, preferably 0.20 $mJ/mm^2$ or less. The peak pressure amplitude of the positive part of the cycle should be above 1.0 and its duration is below 1-3 microseconds.

The treatment depth can vary from the surface to the full depth of the treated tissue. The treatment site can be defined by a much larger treatment area than the 0.10-3.0 cm 2 commonly produced by focused waves. The above methodology is particularly well suited for surface as well as sub-surface soft tissue organ treatments as is found in the regions of the male reproductive system.

The above methodology is valuable in generation of tissue, vascularization and may be used in combination with stem cell therapies as well as regeneration of tissue and vascularization. While the above listed indications cited above are not exhaustive nor intended to be limiting, it is exemplary of the wide range of beneficial uses of low energy and amplitude unfocused divergent, planar or nearly planar shock waves, convergent shock waves, diffused shock waves or a combination of shock wave types in the treatment of humans and other mammals that are infertile or impotent.

A most significant method of preventive medicine can be practiced that is fully enabled by the use of these relatively low amplitude and pressure shock waves. The method includes the steps of identifying high risk patients for a variety of potential infertility or impotence conditions. Such condition could be by way of example ovarian cancer treatments. After identifying a risk prone candidate providing one or a series of two or more exposure treatments with unfocused, divergent, planar or near planar shock waves or convergent far-sighted focused shock waves or diffused shock waves to the treatment site, in this example the region surrounding or in proximity to malignant cells or tumors. Then after treatments the physician can optionally ultrasound visually or otherwise determine the increase in regeneration or vascularization in the treated tissue after a period of time. Assuming an initial baseline determination of the tissue regeneration or vascularization had been initially conducted an estimate or calculation of treatment requirements can be made. If required, the physician can conduct a surgical procedure or alternatively prescribe medications. This procedure can be used for any at risk reproductive condition. After such a surgery or medical drug treatment the surrounding tissues can be post-operatively shock wave treated as well.

The implications of using the (re)generative features of this type of shock wave therapy are any weakened reproductive tissue can be strengthened to the point of reducing or eliminating the risk of irreparable damage or degenerative failure.

The stimulation of growth factors and activation of healing acceleration within the cells of the treated tissues is particularly valuable to cancer patients and other high risk factor subjects exposed to radiation or chemical agents.

Even more striking as mentioned earlier, early prevention therapies can be employed to stimulate tissue or organ modeling to be maintained within acceptable ranges prior to an exposure to a degenerative condition occurring. This is extremely valuable in the prevention of age related infertility for example. The methods would be to identify at risk patients or workers based on family history and exposure risks, and subjecting that patient or worker to therapeutic shock wave therapy for the purpose of stimulating tissue repair or regeneration effectively remodeling the patient's susceptible tissue to be within accepted functional parameters prior to exposure. The objective being to preventively stimulate cellular tissue repairs to pre-emptively avoid a degenerative condition from occurring which may result in the onset of cancer or other reproductive disease which may require invasive surgical procedures.

This preventive therapy is most needed to combat age related loss of function which left untreated results in cellular destruction or any other degenerative conditions within the reproductive system.

The following invention description first provides a detailed explanation of acoustic shock waves or pressure pulses, as illustrated in FIGS. 1-6. As used herein and shown in the figures, an acoustic shock wave is an asymmetric wave with an exceptionally rapid peak rise time and slower return time from the peak amplitude. Historically, these acoustic shock waves or pressure pulses were first used medically to destroy kidney stones. The wave patterns were directed to a focal point at a relatively high energy to blast the concrements into small urinary tract passable fragments.

A whole class of acoustic shock waves or pressure pulses for medical treatments were later discovered that employed low energy acoustic shock waves or pressure pulses. These low energy acoustic shock waves or pressure pulses maintained the asymmetric wave profile, but at much lower energies.

These low energy acoustic shock waves or pressure pulses advantageously could stimulate a substance without requiring a focused beam. The advantage of such an unfocused beam was the acoustic wave could be directed to pass through tissue without causing any cell rupturing which would be evidenced by a lack of a hematoma or bruising. This use of unfocused, low energy acoustic shock waves or pressure pulses provided an ability to treat a large volume of tissue virtually painlessly. Furthermore, the acoustic energy caused a short duration anesthetic sensation that effectively numbs the patient's pain over a period of days with a prolonged reduction in pain thereafter.

The use of low energy acoustic shock waves or pressure pulses that employ a focused beam has been spurred on as a viable alternative to the unfocused low energy shock waves because the focal point being of a small zone of energy has little or a small region of cell damage as the remaining portions of the wave pattern can provide a stimulating effect similar to the unfocused shock waves. Basically, the effect is the same with the users of focused waves achieving the benefits of the unfocused waves, but with a focal point of peak energy in a tiny localised region. So, for purposes of the present invention, the use of "soft waves" those defined by low energy beams will be applicable to both focused and unfocused beams of acoustic shock waves or pressure pulses.

Heretofore such invasive techniques were not used in combination with shock wave therapy primarily because the shock waves were believed to be able to sufficiently pass through interfering body tissue to achieve the desired result in a noninvasive fashion. While this may be true, in many cases if the degenerative process is such that an operation is required then the combination of an operation in conjunction with shock wave therapy only enhances the therapeutic values and the healing process of the patient and the organ such that regenerative conditions can be achieved that would include not only revascularization of the heart or the reproductive organs wherein sufficient or insufficient blood flow is occurring but also to enhance the improvement of ischemic tissue that may be occupying a portion of the organ. This ischemic tissue can then be minimized by the regenerative process of using shock wave therapy in the fashion described above to permit the tissue to rebuild itself in the region that has been afflicted.

The use of these various acoustic shock wave forms can be used separately or in combination to achieve the desired therapeutic effect. Furthermore, such acoustic shock wave forms can be used in combination with drugs, chemical treatments, irradiation therapy or even physical therapy and when so combined the stimulated cells will more rapidly assist the body's natural healing response.

The present invention provides an apparatus for an effective treatment of indications, which benefit from low energy pressure pulse/shock waves having planar, nearly plane, convergent or even divergent characteristics. With an unfocused wave having planar, nearly plane wave characteristic, convergent or even divergent wave characteristics, the energy density of the wave may be or may be adjusted to be so low that side effects including pain are very minor or even do not exist at all.

In certain embodiments, the apparatus of the present invention is able to produce waves having energy density values that are below 0.1 mJ/mm$^2$ or even as low as 0.000 001 mJ/mm$^2$. In a preferred embodiment, those low end values range between 0.1-0.001 mJ/mm$^2$. With these low energy densities, side effects are reduced, and the dose application is much more uniform. Additionally, the possibility of harming surface tissue is reduced when using an apparatus of the present invention that generates waves having planar, nearly plane, convergent or divergent characteristics and larger transmission areas compared to apparatuses using a target focused shock wave source that needs to be moved around to cover the affected target area. The apparatus of the present invention also may allow the user to make more precise energy density adjustments than an apparatus generating only focused shock waves, which is generally limited in terms of lowering the energy output.

The penile tissue is strengthened, inflammation reduced, nerves regenerated, and stem cells recruited and activated. All acoustic waves, focused and unfocused, spherical, radial, ballistic, etc. could be used for treatments.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A method of treating an appendage of a patient, comprises the steps of:
   placing an acoustic shock wave applicator on a surface of the appendage, wherein said placing the acoustic shock wave applicator includes manually retaining the acoustic shock wave applicator in contact with skin of the appendage;
   placing a gaseous filled membrane at a location on an opposite surface of the appendage relative to a location of the acoustic shock wave applicator, wherein the gaseous filled membrane is integral with a mitten or a glove, wherein the gaseous filled membrane is on a palm side of the mitten or the glove, and wherein said placing the gaseous filled membrane includes donning the mitten or the glove and holding the appendage in contact with the palm side of the mitten or the glove;
   causing one or more acoustic shock waves to be transmitted from the acoustic shock wave applicator through the appendage by activating an acoustic shock wave generator or source coupled to the acoustic shock wave applicator, wherein the one or more acoustic shock waves impinge upon the gaseous filled membrane, thereby reflecting the one or more of the acoustic shock waves back into the appendage.

2. The method of treating the appendage of the patient of claim 1, wherein each of the acoustic shock waves are unfocused and have amplitudes above 0.1 MPa.

3. The method of treating the appendage of the patient of claim 1, wherein:
   the gaseous filled membrane has an internal chamber filled with air, nitrogen or other inert gas; and
   the internal chamber has a thickness of at least 1 cm or more.

4. The method of treating the appendage of the patient of claim 1, wherein the method further comprises the step of: prior to said placing the gaseous filled membrane, applying an acoustic gel to the location on the opposite surface of the appendage to acoustically couple the appendage and the gaseous filled membrane.

5. The method of treating the appendage of the patient of claim 1, wherein the acoustic shock wave applicator is electrohydraulic and has a fluid filled flexible membrane.

6. The method of treating the appendage of the patient of claim 1, wherein the appendage is of one of a hand, a foot, a penis, and a scrotum.

7. The method of treating the appendage of the patient of claim 1, wherein the one or more acoustic shock waves are convergent, divergent, planar, or near planar.

8. The method of treating the appendage of the patient of claim 1, wherein:
   the one or more acoustic shock waves are convergent having one or more geometric focal volumes or points located at a distance X;
   X being defined as the distance from an exit window to the one or more focal volumes or points from the generator or source; and
   the appendage is positioned at the distance X or less than the distance X from the exit window source.

9. The method of treating the appendage of the patient of claim 1, wherein the method further comprises the step of lowering the temperature of the appendage being treated prior to said activating to change tissue impedance of the appendage to improve tissue stimulation.

10. The method of treating the appendage of the patient of claim 1, wherein:
    the mitten or the glove includes a first of material defining a palm region of the glove and at least partially defining a hand-receiving space thereof;
    the mitten or the glove includes a second layer of material attached to the first layer of material to define an interior space between the first and second layers of material;
    and the interior space has the gaseous filled membrane therein.

11. The method of treating the appendage of the patient of claim 1, wherein:
    the gaseous filled membrane is in the form of an air bag having opposing walls jointly defining an interior chamber having a fluid material therein; and
    a surface of at least one of the opposing walls has reflective material thereon.

12. The method of treating the appendage of the patient of claim 3, wherein the gaseous filled membrane has an elastomeric conformable exterior surface that conforms to the shape of the surface of the appendage when holding the appendage in contact with the palm side of the mitten or the glove.

13. The method of treating the appendage of the patient of claim 6, wherein:

the appendage is a penis of an adult post pubertal male;

the patient exhibits erectile dysfunction; and the method further comprises the step of administering a medication to the patient prior to said activating for causing the penis to be erect during said activating.

14. The method of treating the appendage of the patient of claim 10, wherein:

the gaseous filled membrane is engaged with an exterior surface of the first layer of material;

the interior space defined by the first and second layers of material is filled with a fluid that reflects the acoustic shock waves.

15. The method of treating the appendage of the patient of claim 10, wherein:

the appendage is a penis;

the patient exhibits erectile dysfunction; and the method further comprises the step of administering a medication to the patient prior to said activating for causing the penis to be erect during said activating.

16. The method of treating the appendage of the patient of claim 14, wherein:

the appendage is a penis;

the patient exhibits erectile dysfunction; and the method further comprises the step of administering a medication to the patient prior to said activating for causing the penis to be erect during said activating.

17. The method of treating the appendage of the patient of claim 11, wherein:

the appendage is a penis;

the patient exhibits erectile dysfunction; and the method further comprises the step of administering a medication to the patient prior to said activating for causing the penis to be erect during said activating.

* * * * *